United States Patent [19]

Desai

[11] Patent Number: 5,490,836
[45] Date of Patent: Feb. 13, 1996

[54] ENDOSCOPIC SURGICAL INSTRUMENT

[76] Inventor: Ashvin H. Desai, 2338 Walsh Ave., Santa Clara, Calif. 95051

[21] Appl. No.: 329,676

[22] Filed: Oct. 26, 1994

Related U.S. Application Data

[63] Continuation of Ser. No. 25,003, Mar. 2, 1993, abandoned, which is a continuation-in-part of Ser. No. 779,108, Oct. 18, 1991, Pat. No. 5,322,503.

[51] Int. Cl.⁶ .............................. A61N 1/30; A61M 1/00
[52] U.S. Cl. .................. 604/21; 604/33; 604/35
[58] Field of Search ...................... 604/21, 22, 30, 604/32–35, 167, 249, 902; 606/39–41, 45, 46

[56] References Cited

U.S. PATENT DOCUMENTS

| | | | |
|---|---|---|---|
| 557,589 | 7/1896 | Lockwood | 251/349 |
| 1,314,855 | 9/1919 | Carpenter | 604/33 |
| 2,706,660 | 4/1955 | Johnson et al. | 251/348 |
| 3,850,175 | 11/1974 | Iglesias | 606/46 |
| 4,673,393 | 6/1987 | Suzuki et al. | 604/167 |
| 4,760,940 | 8/1988 | Wallace et al. | 251/354 |
| 4,895,565 | 1/1990 | Hillstead | 604/167 |
| 5,071,419 | 12/1991 | Rydell et al. | 604/35 |
| 5,125,910 | 6/1992 | Freitas | 604/249 |
| 5,186,714 | 2/1993 | Boudreault et al. | 604/35 |
| 5,188,591 | 2/1993 | Dorsey, III | 604/249 |
| 5,190,541 | 3/1993 | Abele et al. | 604/35 |
| 5,195,958 | 3/1993 | Phillips | 604/33 |
| 5,197,963 | 3/1993 | Parins | 606/41 |
| 5,219,348 | 6/1993 | Buess et al. | 606/40 |
| 5,230,704 | 7/1993 | Moberg et al. | 604/35 |
| 5,244,459 | 9/1993 | Hill | 604/249 |
| 5,247,966 | 9/1993 | Stevens et al. | 604/249 |
| 5,273,524 | 12/1993 | Fox et al. | 604/21 |
| 5,295,956 | 3/1994 | Bales et al. | 604/35 |

FOREIGN PATENT DOCUMENTS

327410  8/1989  European Pat. Off. .

*Primary Examiner*—C. Fred Rosenbaum
*Assistant Examiner*—Frank Wilkens, III
*Attorney, Agent, or Firm*—David H. Jaffer

[57] ABSTRACT

An endoscopic surgical instrument 20 includes an irrigation port 21 and an evacuation port 22. Each port, 21 and 22, is connected through independent valves 23 and 24, respectively to a single access conduit 25. The connection between the valves 23 and 24 and conduit 25 is along connector tubes 23a and 24a. The access conduit 25 leads from the valves and their respective valve conduits to a probe connector 26. This probe connector 26 is designed to receive one end, the locating end 27, of a surgical probe 28 which would be used during microsurgical procedures. The surgical instrument 20 also includes a port 31 which allows the surgeon to insert microsurgical instrumentation (not shown) along the access conduit 25 and the bore of the hollow probe 28 to exit from the end 32 thereof. The port 31 should provide a fluid-tight seal when no microsurgical instrumentation is being used with the surgical instrument 20. This will prevent fluid which may be moving along the access conduit 25 to or from the patient, from leaking.

2 Claims, 5 Drawing Sheets

Fig_9   Fig_13

Fig_10   Fig_11   Fig_12

ENDOSCOPIC SURGICAL INSTRUMENT

This is a continuation of application Ser. No. 08/025,003 filed on 03/02/93, abandoned which is a continuation-in-part of Ser. No. 07/779,108 filed 10/18/91. Ser. No. 07/779,108 is now U.S Pat. No. 5,322,503.

BACKGROUND OF THE INVENTION

1. Field of the Invention

This invention relates to a surgical instrument and more particularly to an instrument with the capability for automatic irrigation and evacuation of a patient during Laparoscopic or Endoscopic surgical procedures. This invention also relates to irrigation/evacuation control valves for such an instrument.

2. Brief Description of the Prior Art

Laparoscopic/endoscopic surgical procedure allows a surgeon to see inside the body of a patient without the necessity of large incisions. This reduces the chances of infection and other complications related to large incisions. The laparoscope (or endoscope) further allows the surgeon to manipulate microsurgical instruments within its housing without impeding the surgeon's view of the area under consideration.

During these surgical procedures it is desirable for as few lines as possible to enter the body of the patient. This reduces the size of the incision the surgeon needs to make. It follows from this that the greater the number of functions provided by a single instrument or the greater the number of instruments able to be passed through a single line entering the patient's body, the better.

Furthermore, in certain procedures it may be desirable to irrigate the area under consideration. This is turn necessitates the evacuation of the irrigation fluid or, when bleeding has occurred, the blood or fumes or tissue residue generated by the surgical procedure.

From what has been said above it should be apparent that it is preferable for both irrigation and evacuation to be conducted along a single conduit which, in turn, acts as an access line for surgical instruments.

A typical device which is used in laparoscopic procedures is an electrosurgical probe. Typically such a probe will comprise an radio frequency energy conductive tube covered with a dielectric material such as polyolefin. At one end, for convenience called the operational end, each probe could have any one of a number of functionally shaped electrodes. In addition a probe could have its end formed specifically for irrigation and/or evacuation.

As the electrodes at the end of the probe are not necessarily symmetrical about the longitudinal axis of the probe, it is desirable for the probe to be mounted on its supporting instrument to permit rotation thereof about this axis. This would allow the manipulation of the operational end of the probe without unnecessary and inconvenient manipulation of the surgeon's arm. In addition, as a variety of electrode shapes are available to the surgeon it is desirable for these probes to be interchangeable.

Furthermore, any valves controlling the evacuation and irrigation procedures should be constructed so as to minimize the possibility of the valve malfunctions if, for example, any tissue or blood coagulates around their moving parts. Similarly if any of the instrumentation is to be reusable, such instrumentation, including the valves, should be capable of being efficiently cleaned by, for example, flushing.

U.S. Pat. No. 4,668,215 (Allgood) discloses a valve for switching between an evacuation and an irrigation conduit and allowing both such evacuation and irrigation to be done via a single line entering the patient. The mechanism for switching between the irrigation, evacuation and closed configurations is by means of a L-valve or T-valve. This patent, in another embodiment thereof, further provides for a piston valve for making an on-off connection between an evacuation port and the line leading into the patient.

The L- and T-valves have the disadvantage that they must be manipulated by rotation by the surgeon, usually using his/her free hand. The piston valve disclosed in this patent has the disadvantage that it has many areas where blood and tissue accumulation and coagulation can occur which may result in the malfunctioning of the valve. In addition, the piston valve has numerous "dead" areas where fluid flow would not occur. This precludes the device from being effectively cleaned by commonly used flushing techniques. Finally, the Allgood patent does not disclose a single body for housing an evacuation/irrigation control valve together with a housing for laparoscopic and microsurgical instrumentation.

Figure 1:
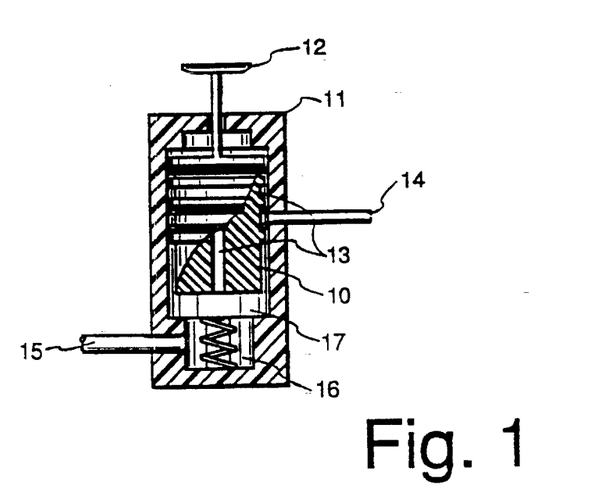
FIG. 1 is a partial sectional elevation through a prior art piston valve.

A surgical valve that the applicant is aware of is the piston valve illustrated in FIG. 1 of the accompanying drawings.

In this valve a piston 10 is located within a cylinder 11. The piston 10 can be moved along the bore of the cylinder 11 by means of a plunger 12, from a closed position (as shown) to an open position in which a conduit 13 is aligned with an access port 14. This allows fluid flow along a path to or from access port 14, via conduit 13 and space 16 from or to a further port 15. Upon release of the plunger 12 the piston 10 returns to its closed position under action of a spring 17.

This valve, although easy to use, has the disadvantage that blood and tissue accumulation occurs in space 16 and clogs both the space and the spring 17. This may result in undesirable over-evacuation or irrigation of the patient during surgical procedures.

OBJECTS OF THE INVENTION

It is therefore an object of this invention to provide a surgical instrument which includes control means to allow for the irrigation and evacuation of a patient during microsurgical procedures, with both irrigation and evacuation being performed along a single line into the patient. The instrument should also act as a mounting for electrosurgical probes and microsurgical instruments.

A further object of the invention is to provide a configuration for an instrument which, depending on the material it is constructed of, can be both disposable and non-disposable. In the event that the instrument is non-disposable it is an object of the invention to provide the instrument with conduits, access parts and valves which can easily be cleaned by means of commonly used flushing techniques.

Finally it is an object of this invention to provide an instrument which can be controlled using only one hand of the user.

SUMMARY OF THE INVENTION

According to this invention, an endoscopic surgical instrument comprises an irrigation and an evacuation port, each port being connected through independent valves to a single access conduit; a probe connector located at one end of the access conduit, the probe connector being for receiving and retaining a hollow surgical probe; and a radio frequency connector which exits into the access conduit in such a manner so as to make radio frequency connection with a probe received by the probe connector.

Preferably the connector for receiving an end, for convenience called the locating end, of the probe would be in the form of a receiving bore in the access conduit which would include a plurality of O-rings which provide a fluid-tight seal around the locating end of the probe. These O-rings also function to retain the probe in the receiving port while allowing the probe to be rotated. In one embodiment of the invention, the O-rings are, instead of being located within the receiving bore of the access conduit, located about the locating end of the probe.

This invention also provides for a valve, for use as either an evacuation or an irrigation valve, the valve comprising a housing, an activator connected to the housing, at least a first and a second valve access conduit, both of which exit into the housing and a fluid impervious seal mounted within the housing such that activation of the activator causes the first valve conduit to move axially relative to the seal and the second valve conduit such that the seal is disengaged and the conduits are placed in direct fluid communication with each other.

Typically, the instrument of the invention would contain two of the above described valves. One valve would act as an evacuator control while the other valve would act as an irrigation control. Both valves communicate into a single access conduit which, when the instrument is in use, leads into the patient via the receiving bore and the hollow interior of the electrostatic probe.

Preferably the endoscopic surgical instrument of the invention is in the form of a pistol with the "barrel" portion thereof having, at one end thereof, the receiving bore for the locating end of the endoscopic probe and, at the other end thereof, the access port for the microsurgical instruments.

The valves for controlling the evacuation and irrigation procedures may be mounted in the "handle" portion of the pistol-shaped instrument. The valves may be mounted alongside one another in the handle portion and may protrude therefrom to allow finger control by the surgeon using the instrument.

These and other objects and advantages of the present invention will no doubt become apparent to those skilled in the art after having read the following detailed description of the preferred embodiment which is illustrated in the several figures of the drawing.

DETAILED DESCRIPTION OF PREFERRED EMBODIMENTS

Figure 2:
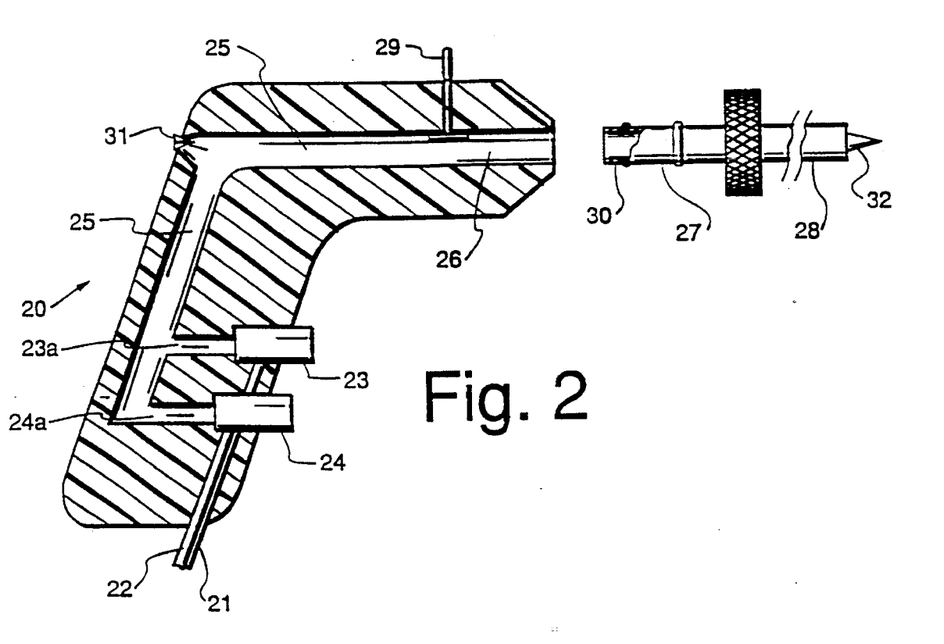
FIG. 2 is a diagrammatic section through a semi-exploded elevation of one embodiment of the endoscopic surgical instrument of the invention.

In FIG. 2 of the accompanying drawings, the endoscopic surgical instrument of the invention is generally indicated as 20. The instrument 20 is shown to include an irrigation port 21 and an evacuation port 22. Each port, 21 and 22, is connected through independent valves 23 and 24, respectively, to a single access conduit 25. The connection between the valves 23 and 24 and conduit 25 is along connector tubes 23a and 24a.

The access conduit 25 leads from the valves and their respective valve conduits to a probe connector 26. This probe connector 26 is designed to receive one end, the locating end 27, of a surgical probe 28 which would be used during microsurgical procedures. The connection 26 is described in more detail with reference to FIGS. 4 and 5 hereafter.

At or near the probe connector 26, a radio frequency connector 29 is located. As illustrated, this is in the form of a banana connector. The advantage of a banana connector is that it is an industry standard and can be used for connecting the instrument 20 to regular frequency supply sources manufactured by a number of different manufacturers.

The radio frequency connector 29 exits into the access conduit 25 where it makes connection with a point 30, on the locating end 27 of a probe 28 received by the probe connector 26.

The surgical instrument 20 also includes a port 31 which allows the surgeon to insert microsurgical instrumentation (not shown) along the access conduit 25 and the bore of the hollow probe 28 to exit from the end 32 thereof. The port 31 should provide a fluid-tight seal when no microsurgical instrumentation is being used with the surgical instrument 20. This will prevent fluid, which may be moving along the access conduit 25 to or from the patient, from leaking.

Figure 3A:
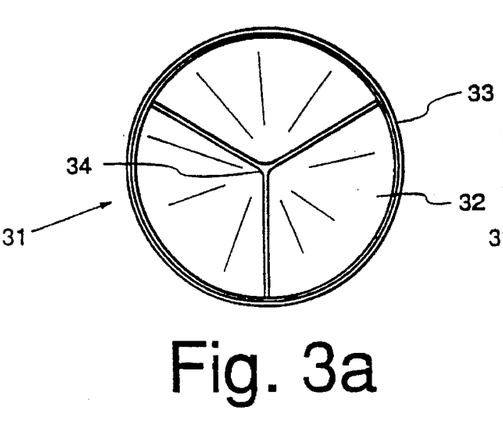
FIG. 3 is an illustration of a tricuspid valved access port illustrated in plan (a) and elevation (b) views.
Figure 3B:
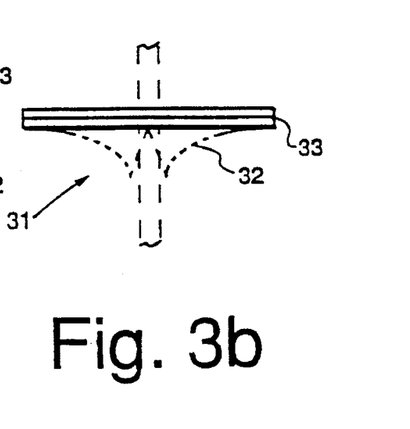

Typically, the access port 31 is in the form of a commercially available tricuspid valve as illustrated in FIGS. 3(a) and (b). In these figures, the valve 31 is shown as being constituted by three segments 32 which in plan view are wedge-shaped and which together form the disc shaped sealing portion of the valve. The segments 32 are held together by means of a circumferencial ring 33 which biases the three segments 32 together to form a fluid-tight seal. In use, the microsurgical instrumentation are inserted through the valve at a point 34 where the apexes of the segments 32 come together. This insertion forces the elements of the valve apart to allow ingress of the microsurgical instrumentation. The effect thereof is shown in broken lines in FIG. 3(b). When the instrumentation is removed from the valve 31, the segments 32 are pulled together to form the seal.

Figure 4A:
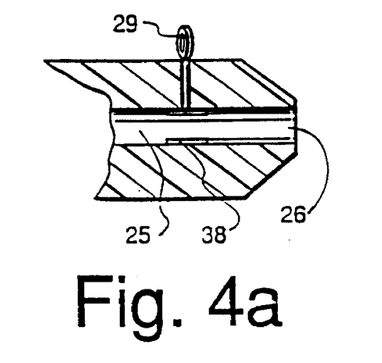
FIG. 4 is a section through a receiving bore of the instrument illustrating one way of locating a probe in the bore.
Figure 4B:
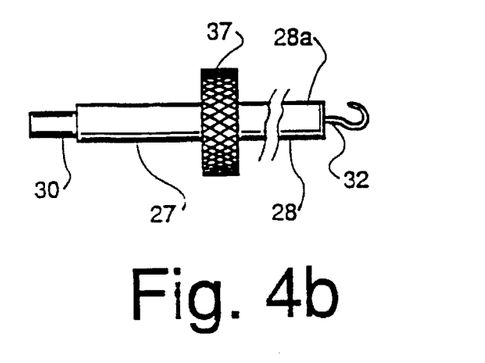

In FIG. 4 the probe connector 26 is shown to be constituted by a receiving bore which is coaxial with the fluid access conduit 25. In practice, the diameter of this bore would be the same as that of the access conduit 25 and would be sized to receive the locating end 27 of the probe 28 in a relatively close fit. Within the bore forming the probe connector, a plurality, typically two, O-rings 36 are located. When the locating end 27 is inserted into the bore 26 these O-rings provide a snug, fluid-tight seal about the end 27. Once the locating end 27 of the probe is received within the bore 26 it is capable of being rotated about its longitudinal axis, by means of a knurled rotation knob 37 located between the locating end 27 and the operational end 32 of the probe 28.

The probe 28 would typically be made of a electrostatic conductive material coated with a non-conductive material such as heat shrink polyolefin. Electrostatic/radio frequency energy is passed along the probe 28 from the radio frequency connector 29 via electrostatically conductive plates 38 located within the bore of the probe connector 26 and onto the end 30 of the probe 28. The end 30 is so designed such that when the locating end 27 of the probe is received by the probe connector 26, electrostatic connection is made between the plate 38 and the connector 30. This allows the surgeon to pass energy into the patient being operated on.

Figure 5A:
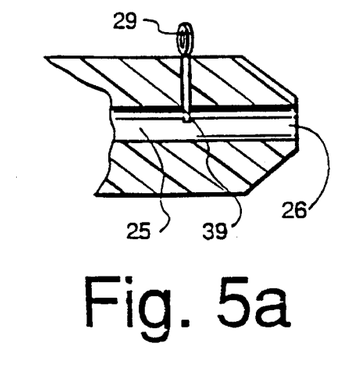
FIG. 5 is a section through a similar receiving bore showing a different way of locating a probe in the bore.
Figure 5B:
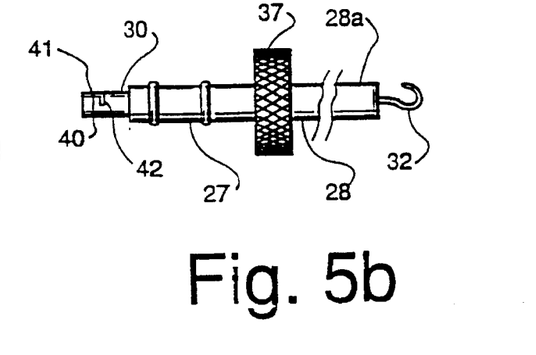

An alternative radio frequency connector is illustrated in FIG. 5. In this case, the banana connector 29 exits into the bore 26 in the form of a pin 39. In the conductive end 30 of the probe 28 an L-shaped slot 40 is formed. As the probe 28 is inserted into the receiving bore 26, the pin 39 engages the axially-orientated leg 41 of the L-shaped slot 40. When the probe can be inserted no further along the bore it is twisted, in this case in an anti-clockwise direction, such that the pin 39 and the axially transverse leg 42 of the L-shaped slot 40 engage each other to lock the probe 28 into position. In this embodiment the probe 28 cannot be rotated by means of the knurled knob 37.

FIG. 5 further illustrates an alternative positioning of the O-rings 36. In this case they are located on the locating end 27 of the probe 28.

From FIGS. 4 and 5, although not shown, it will be apparent that the diameter of the operational shank 28a of the probe 28 can be variable. Typically, the probe, as shown, would have a diameter of 5 mm. This diameter can, however, be increased to 10 mm which would be close to the diameter of the locating end 27 of the probe, as well as that of the internal bore diameter of the access conduit 25. The advantage of 10 mm diameter probes is that the evacuation of removed tissue and objects such as the gall-stones can be more effectively achieved. Obviously, when the bore of the operating shank 28a of the probe, the locating end 27 and the access conduit 25 are all 10 mm in diameter, the diameter of the evacuation port 22 and its related valve 24 and connector tube 24a must also be 10 mm.

In FIG. 6(a) to (i), a number of different electrode shapes are illustrated. These electrode tips would be located on the operating end of the probe 28.

Figure 6:
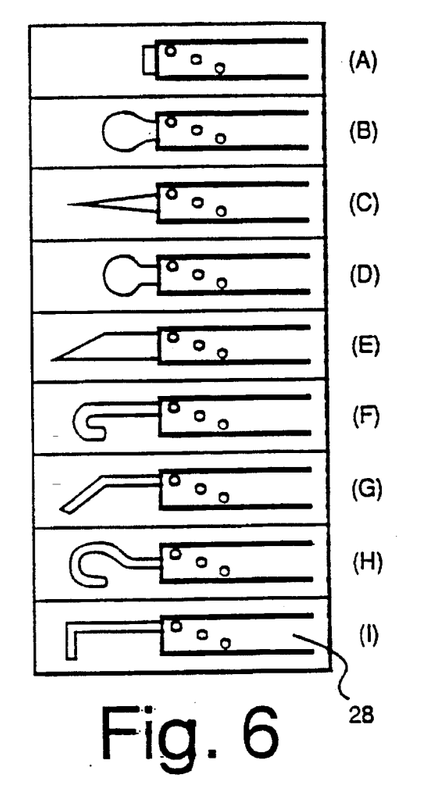
FIG. 6 illustrates in (a)-(i) various electrostatic probe operational ends.

As can be seen from the figure, a number of the tips are not symmetrical about the longitudinal access of the probe 28. It is for this reason that it is desirable for the probe 28 to be mounted on the instrument in such a manner to allow for a rotation of the probe about its longitudinal axis. As has been previously indicated, this will give the surgeon the opportunity of rotating any non-symmetrical tips, inside the patient, without having to rotate his or her wrist.

This invention extends also to an electrostatic probe 28, substantially as described in any of the FIGS. 4 to 6.

Figure 7:
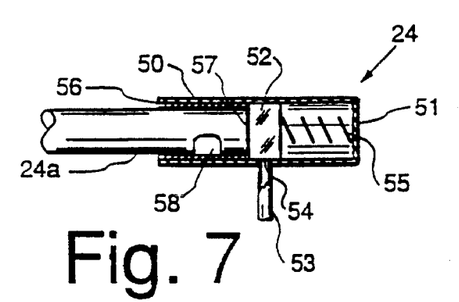
FIG. 7 is a section through a valve according to the invention with the valve being in the shut position.
Figure 8:
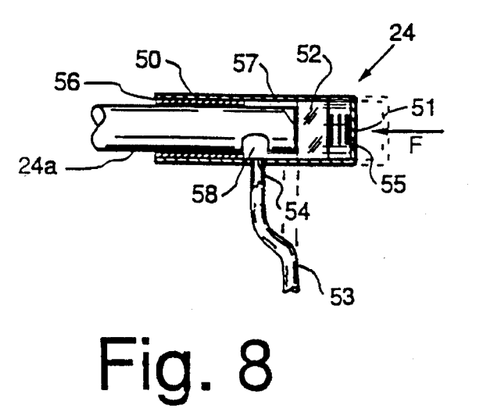
FIG. 8 is the valve of FIG. 7 in the open position.

The details of one type of irrigation/evacuation valve are illustrated in FIGS. 7 and 8. The valve 24 indicated in both figures comprises a housing constituted by a hollow tube 50 and an activator in the form of a button 51 formed integrally with the tube 50. A fluid impervious seal 52 is located within the tube 50. Referring specifically to FIG. 7, in which the valve is shown in the shut position, it can be seen that the seal 52 lies between a first valve conduit 53 which leads to the evacuation port 22 (not shown) and a second valve conduit in the form of connector tube 24a which leads into the primary access conduit 25 of the surgical instrument. In effect, the seal 52 prevents the conduits 53 and 24a from being in communication with each other.

The first valve conduit 53 is mounted onto the wall of the tube 50 and opens into the interior of the tube 50 through a hole 54. Between the seal 52 and the button portion 51 of a tube 50, a spring 55 is located. On the side of the seal 52, opposite to which the spring is located, a tubular insert 56 is located. This tubular insert has a snug but slidable fit over the outer wall of the second valve conduit 24a as well as a tight, fluid impervious fit into the inner bore of the tube 50. This tube 56 acts as a stop which prevents the spring 55 from pushing the seal 52 out of the hollow tube 50.

To open the valve, as is illustrated in FIG. 8, an activating force, applied along a line F to the button 51, will cause the button to move from the position indicated in broken lines to the illustrated open-valve position. As the button moves, so does the hollow tube 50, taking the first valve conduit 53 along with it. In addition, the leading edge 57 of the second valve conduit 24a bears against the seal 52 causing the seal to move relatively to the tube 50. This in turn disengages the seal from sealing the hole 54 in the wall of the tube 50. The movement of the first valve conduit 53, relative to the second valve conduit 24a, places the respective openings 54 and 58 of these two conduits in fluid communication with each other thereby allowing an unobstructed fluid flow along both access conduits.

Upon release of the force on the button 51, the bias of the spring 55 will return the valve to its shut position.

It is evident from the construction of the valves illustrated in FIGS. 7 and 8 that they can be readily cleaned by commonly used cleaning such as flushing. In addition, the valves have almost no areas where blood and tissue accumulation and coagulation can occur, and if such accumulation and coagulation does occur the valves cannot be jammed in the open position. This is because the spring biasing the valve into its closed position is located in an effectively sealed area. Furthermore these valves have been tested to a pressure of up to 100 psi without the integrity of the valve seal being adversely affected.

Figure 9:
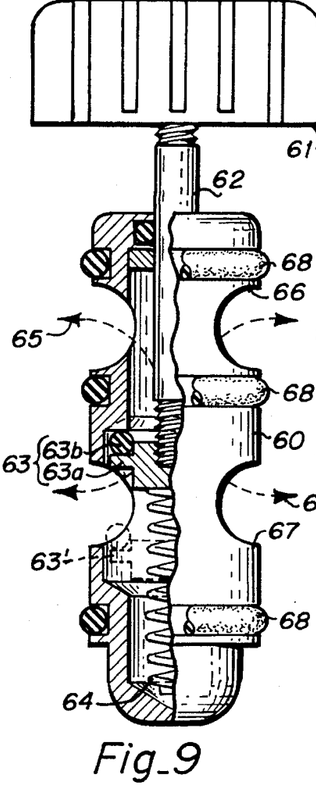
FIG. 9 is a partial section through a different type of valve also suitable for use in the instrument of the invention.

An alternative form of valve, to that illustrated in FIGS. 7 and 8 above, is shown in FIG. 9. In the figure the valve is shown to include a generally cylindrical valve body 60, an activating button 61 and a plunger 62. A hollow bore runs down the center of the valve body 60 and contains the valve seal 63. The valve seal 63 is made up of a circular washer 63a and a sealing O-ring 63b and is screwed onto the bottom of plunger 62. The valve seal 63 is biased into its illustrated sealing position by means of a spring 64 located in the bottom part of the valve body 60.

To open the valve, the button 61 is depressed so that the plunger 62 forces the valve seal 63 downwards against the bias of the spring 64 to a position shown in broken lines 63', in the figure. As a result, a fluid path, indicated by arrows 65, is opened between an upper pair of cutouts 66 and a lower pair of cutouts 67. Each pair of cutouts opens into the hollow bore in the center of the valve body 60 and, when this valve is inserted into the surgical instrument, into either an evacuation or irrigation conduit. Closure of the valve is achieved by releasing the button and allowing the spring 64 to return the valve seal 63 to the sealing position.

One advantage of this embodiment of the valve is that it is easily removed from and inserted into the surgical instrument of the invention. Accordingly the valve can easily be removed for cleaning or disposal and replacement. This is further illustrated below with respect to FIG. 13. It is sufficient here to mention only that the surgical instrument is provided with a receiving bore for each valve and that the valve includes a plurality (in this case 3) O-rings 68 which, when the valve is inserted into its respective receiving bore, provide a number of fluid tight seals against the inside of the bore.

Either of the two types of valve described in FIGS. 7 to 9 can be used on the instrument 20. Typically one valve would act as an evacuation valve while the other as an irrigation valve. Different types of arrangements of valves and valve activation means are illustrated in the following 4 figures.

Figure 10:
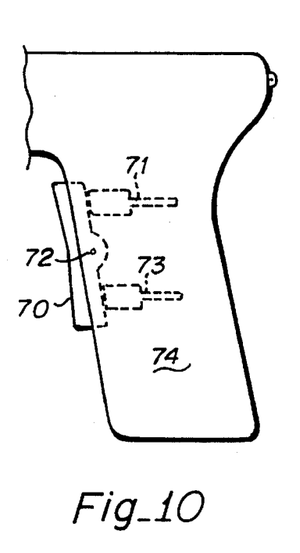
FIGS. 10, 11, 12 and 13 are diagrammatic illustrations showing various configurations of valve operating buttons and triggers.

One way of activating the valve is by means of a rocker-shaped trigger 70 illustrated in FIG. 10. The trigger 70 is pivotally mounted on a point 72 on the handle 74 of the pistol. Depressing the trigger 70 to operate the irrigation valve 71 would not interfere with the operation of the evacuation valve 73. Similarly, operation of the trigger 70 to operate the evacuation valve 73 would in no way effect the operation of the irrigation valve. It is evident from this figure that it would be impossible to operate both the irrigation and the evacuation valve simultaneously thus preventing wasteful and undesirable simultaneous evacuation and irrigation.

Figure 11:
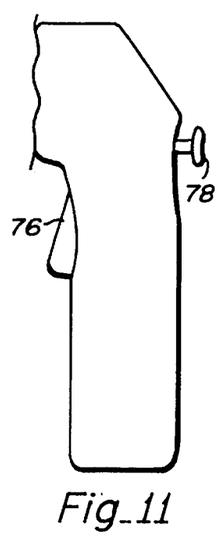

In FIG. 11 a trigger mechanism 76 is shown for operation of only one of the buttons. The other button 78 would be located for operation by means of the surgeon's thumb in a position removed from the trigger 76. This could, for example, be near the top end of the handle portion of the instrument.

Figure 12:
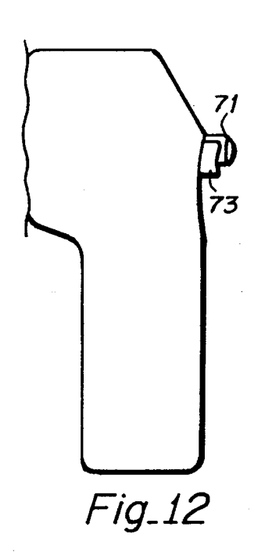

Yet a further positioning of the buttons 71 and 73 is indicated in FIG. 12. In this instance, the buttons protrude from the top rear of the pistol handle and are located side-by-side. To prevent confusion between evacuation and irrigation procedures, the tops of the buttons have different shapes. So, for example, the button to manipulate the evacuation valve could be concave while the button for manipulating the irrigation valve could be convexly shaped.

Figure 13:
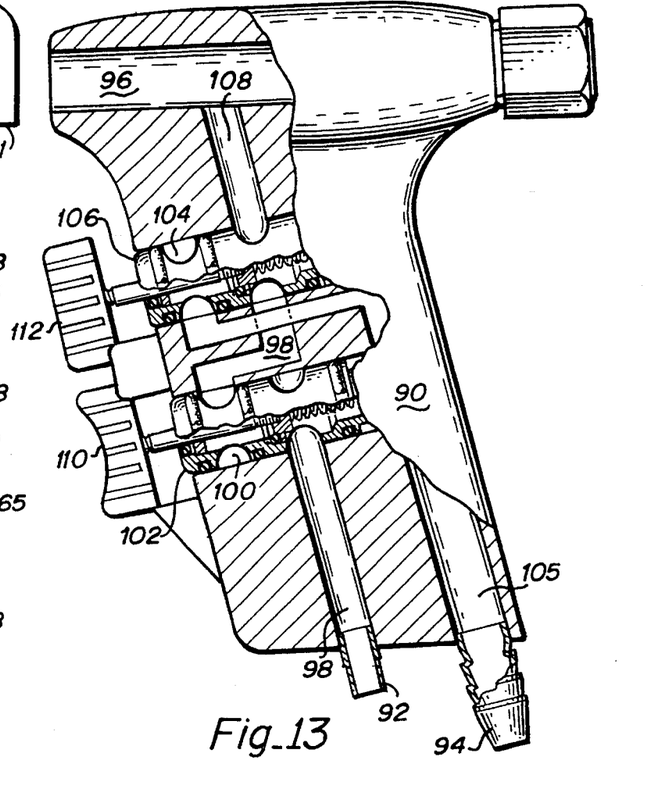

FIG. 13 illustrates still another arrangement of buttons and valves, in this case an arrangement particularly suited to the valve shown in FIG. 9.

In this figure only the pistol grip 90 of the surgical instrument of the invention is shown. An irrigation port 92 and evacuation port 94 enter the pistol grip 90 at the bottom of its handle portion. The ports 92, 94 are, in use, respectively connected to irrigation and evacuation conduits (not shown) and, to this end, suitable connectors, as illustrated, are provided.

The irrigation port 92 communicates with the main access conduit 96 (referenced as 25 in FIGS. 2, 4 and 5) along an irrigation conduit 98 which extends from the irrigation port 92 and into the rear of the bore 100 which houses an irrigation valve 102. From there it extends along the bore 100 to a point near the front of the bore from where it exits into the body of the grip 90 to enter rear of the bore 104 which houses an evacuation valve 106. the irrigation conduit extends directly across the bore 104 at this point and becomes a central conduit 108 which communicates with the access conduit.

On the other hand, the evacuation port 94 communicates with an evacuation conduit 105 which extends along the pistol grip 90 directly into the front of the bore 104, down to the bore 104 to its rear from where it exits into the central conduit 108.

In the position shown, both the irrigation and evacuation valves 102, 106 respectively, are shown in the off or shut configurations and neither evacuation or irrigation can take place. Should irrigation of the patient be required, the dish-shaped irrigation button 110 is depressed and the valve 102 opens (i.e. its valve seat moves to the right in the drawing) to allow irrigation fluid to pass along the irrigation conduit 98 and into the bore 104. In this bore 104 the evacuation valve 106 is in the off configuration. However, a fluid path exists across the pair of cutouts (67 in FIG. 9) and therefore the irrigation fluid can pass through the body of the valve 106 and into the central conduit 108 and, from there, into the access conduit 96.

When evacuation is desired the irrigation button 110 is released and the spring associated with the irrigation valve 102 biases it into the shut or off configuration. Thereafter the flat topped evacuation button 112 is depressed to open the evacuation valve 106. This allows the patient to be evacuated along the main access conduit 96, into the central conduit 108, then from the rear to the front of the bore 104 and, from there, out along the evacuation conduit 105.

As has been indicated earlier, the valves 102, 106 are easily inserted into and removed from their respective bores 100, 104. This allows the pistol grip 90 (which is typically stainless steel and is reusable) to be cleaned efficiently. The valves, typically being of plastic and being difficult to clean, can be discarded and replaced with new valves.

Figures 14, 15, 16:
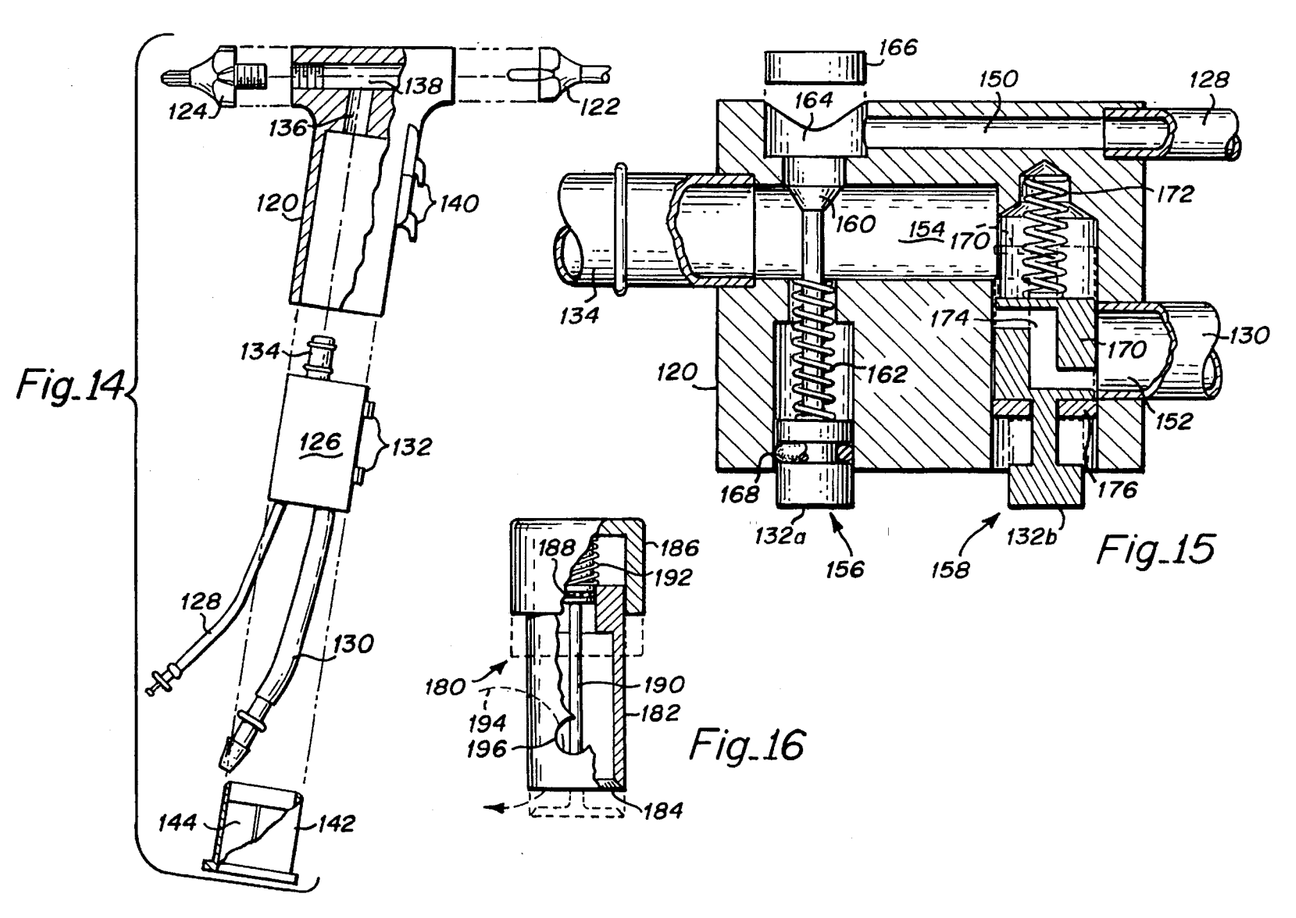
FIG. 14 is an exploded view of an alternative embodiment of the surgical instrument of the invention illustrating a disposable valve cartridge.
FIG. 15 is a cross section through the disposable valve cartridge illustrated in FIG. 14.
FIG. 16 is a partially sectioned view of another type of valve which can be used in the surgical instrument of the invention.

A variation on this theme of discardable valves is illustrated in FIG. 14. In this figure the surgical instrument is shown to include a pistol grip 120, a surgical probe 122, which can be screwed into the front of the pistol grip 120 and a radio frequency connector 124 which screws into the back of the grip 120.

The instrument also includes a removable (and disposable) valve cartridge 126. The cartridge 126 includes an irrigation pipe 128 and an evacuation pipe 130 both of which are individually operated by valves (as will be further illustrated in FIG. 15) under action of button-shaped actuators 132. Both the irrigation and evacuation pipes communicate into a single conduit (not shown) which runs down the center of a male connector fitting 134. Where the cartridge 120 is inserted into the grip 120 the connector 134 fits into the base of a central conduit 136 which, in turn, opens up into the main access conduit 138 of the instrument. When the cartridge 120 is located in the grip 120 the actuators 132 are located directly below a pair of operating triggers 140 which can be used to operate the irrigation/evacuation procedures described before.

Finally, when the cartridge 120 is in place, it is held there by means of a retainer clip 142 which clips in behind the cartridge 120. The retainer clip 142 has apertures 144 formed in it to allow the irrigation and evacuation pipes 128, 130 to pass through it.

Although it will be apparent that the valve types described above are also suitable for use in the cartridge 120, a further valve configuration is illustrated in FIG. 15, which illustrates the cartridge 120 in greater detail.

In this figure, the cartridge 120 is shown to include an irrigation conduit 150 and an evacuation conduit 152, both of which lead to a central access conduit 154 which extends down the center of the male connector 134. Irrigation and evacuation procedures are controlled by irrigation and evacuation valves 156 and 158, respectively.

The irrigation valve 156 consists of a valve seal 160 mounted onto a stem which is screwed into an activator button 132a. A fluid tight seal is provided for the valve 156 by an O-ring 168 mounted onto the cap 132a. The valve seal 160 seals against a valve seat, formed at the junction between the irrigation conduit 150 and the central access conduit 154 and is held in the sealing position (as shown) by a spring 162.

Access to the valve seat is through a hole 164 formed into the top (as shown in the drawing) of the cartridge 120. This hole 164 can be closed off with a cap 166 and allows the irrigation valve 156 to be inserted into the cartridge 120. This is done by inserting the valve seal 160 and its associated stem into the hole 164 from above and inserting the spring 162 from below. Thereafter the cap 132a can be screwed onto the stem to hold the entire valve 156 in place.

To operate an irrigation procedure the button 132a is depressed to move the valve seal 160 clear of its seal to open a fluid path between the irrigation conduit and the central access conduit. Releasing the button 132a causes the spring 162 to force the seal 160 back into its seat thereby automatically shutting the valve.

The evacuation valve 158 is of a different construction. In this valve 158, the valve seal 170, in its off position as shown, seals the mouth of the evacuation conduit 152.

In operation, the seal 170 is moved under action of a plunger and evacuation button 132b from the position shown to a position 170' in which an end of a conduit 174, formed through the seal 170, aligns with the central access conduit 154. At the same time the other end of the conduit 174 is aligned with the evacuation conduit 152 and evacuation can be accomplished. By releasing the button 132b, the spring 172 biases the seal 170 back into its sealing position.

Assembly of this evacuation valve 158 is by inserting the entire valve mechanism into its valve bore and sealing a collar 176 in the bore.

As has been indicated with reference to FIG. 14, the cartridge 120 is of the disposable type and is intended for use only once. Accordingly the considerations of valve flushing (during cleaning) are not entirely applicable here.

In FIG. 16 yet another type of valve, which can be used as either an irrigation or an evacuation valve, is illustrated.

The valve, generally indicated as 180, is shown to include a hollow cylindrical valve body 182 which is sealed at its lower end by a valve seal 184 and at the other by an activator button 186. The activator button 186 seals against the valve body with an O-ring 188 and is connected to the valve seal 184 by means of a plunger 190.

To open the valve 180, the button 186 is depressed against the bias of a spring 192 to move the valve seal 184 to the position indicated in broken lines. This opens a fluid path 194 between an opening 196 formed in the sidewall of the valve body and its lower end. Releasing the button 186 allows the spring 192 to force the seal 184 back into the closed position.

One advantage of this valve is that it is very simple and cheap to manufacture and can, therefore, readily be disposed of.

Finally, it will be apparent to anyone skilled in the art, that the surgical instrument of this invention could be made from any suitable material. In the event that the instrument is intended for use only once, some form of plastic material could be used. Alternatively, for repetitive use of the instrument, the instrument can be made of a more durable material such as aluminum.

Although the present invention has been described above in terms of a specific embodiment, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. An endoscopic surgical instrument comprising:
   a) a single access conduit including
      i) a first end having a probe connector for attaching a surgical probe thereto, and
      ii) an opposite end having a port for insertion of surgical instrumentation;
   b) a valve cartridge including
      i) a body portion,
      ii) an irrigation input connector for receiving fluid into said body portion,
      iii) an evacuation output connector for expelling fluid and body tissue from said body portion,
      iv) a male connector fitting for transmission of fluid from said body portion, and for receiving fluid and body tissue into said body portion,
      v) a first valve providing fluid direction within said body portion for interconnecting said male connector fitting to said irrigation input connector, and having a manually operable push button activation means,
      vi) a second valve providing fluid direction within said body portion for interconnecting said male connector fitting to said evacuation output connector, and having a manually operable push button activation means; and
   c) a pistol grip extending from said single access conduit, said pistol grip including
      i) a chamber formed within said pistol grip,
      ii) a cartridge access opening formed through a wall of said pistol grip to said chamber for slideably receiving said valve cartridge therein,
      iii) a central conduit connecting said chamber to said access conduit, and for making slidable connection with said male connector fitting, said central conduit for passage of fluids to said single access conduit from said body portion, and for passing fluids and body tissue from said single access conduit to said body portion, and
      iv) activation means operable through a wall of said pistol grip for activating said push buttons.

2. An endoscopic surgical instrument comprising:
   a) a single access conduit having one end configured as a probe connector for attaching a surgical probe thereto, and having a port for insertion of surgical instrumentation at an opposite end; and
   b) a pistol grip extending from said single access conduit, said pistol grip including
      i) an irrigation input means for receiving irrigation fluid,
      ii) an evacuation output means for expelling fluid and body tissue,
      iii) a central conduit for passage of fluids to said single access conduit from said pistol grip, and for passing fluids and body tissue from said single access conduit to said pistol grip, iv) valve means for operator selectable connection of said irrigation input means to said central conduit, and for operator selectable connection of said evacuation output means to said central conduit, and wherein said valve means includes first and second valve bores extending into said pistol grip from an exterior surface, each said valve bore having a bore diameter and a bore depth, said bore diameter of said first valve bore having a first opening in said bore diameter at a first depth in said first bore from said exterior surface for providing fluid access to said central conduit, and a second opening diametrically opposite said first opening leading to a first conduit, and a third opening located at a second depth in said first bore, leading to a second fluid conduit, and said second bore having a first opening at said first depth, leading to a third fluid conduit, and having a second opening in said bore diameter located at said second depth leading to said first fluid conduit making fluid interconnection with said second opening of said first bore, and said valve means further having first and second valve assemblies for insertion in said first and second bores, each of said valve assemblies having a cylindrical body having a valve diameter dimensioned for a sliding fit in said bore diameter, and having an opening on one end of said body to an elongated chamber within said cylindrical body, said body having first and second diametrically opposed openings into said chamber at said first depth from said opening, and having third and fourth diametrically opposed openings at said second depth, and said valve assembly having a spring loaded plunger activated valve means located between said first depth and said second depth inside said chamber for selectably sealing or connecting a lower first chamber portion accessed by said first and second openings, from a second chamber portion accessed by said third and fourth openings, and said plunger activated valve means having a plunger rod extending from outside said body, having an O-ring seal means sealing said opening around said plunger rod, and said assembly having O-ring seal means for sealing said valve diameter to said bore diameter, said O-rings located before said second depth and between said second depth and said first depth, and after said first depth.

* * * * *